(12) United States Patent
Persson

(10) Patent No.: US 7,780,643 B2
(45) Date of Patent: Aug. 24, 2010

(54) ABSORBENT ARTICLE HAVING X-SHAPED SHAPING ELEMENT

(75) Inventor: Cilla Persson, Gothenburg (SE)

(73) Assignee: SCA Hygiene Products AB, Gothenburg (SE)

( * ) Notice: Subject to any disclaimer, the term of this patent is extended or adjusted under 35 U.S.C. 154(b) by 329 days.

(21) Appl. No.: 11/024,814

(22) Filed: Dec. 30, 2004

(65) Prior Publication Data

US 2005/0143703 A1 Jun. 30, 2005

Related U.S. Application Data

(60) Provisional application No. 60/533,075, filed on Dec. 30, 2003.

(51) Int. Cl.
*A61F 13/539* (2006.01)
(52) U.S. Cl. .................. 604/385.101; 604/385.23
(58) Field of Classification Search ............ 604/385.01, 604/385.101, 384, 385.14, 385.23, 385.27
See application file for complete search history.

(56) References Cited

U.S. PATENT DOCUMENTS

| | | | | | |
|---|---|---|---|---|---|
| 810,128 | A | * | 1/1906 | Green | 604/378 |
| 1,352,774 | A | * | 9/1920 | Angier | 604/385.01 |
| 1,866,220 | A | * | 7/1932 | Norton | 604/401 |
| 2,986,780 | A | * | 6/1961 | Bletzinger | 264/518 |
| 3,104,684 | A | * | 9/1963 | Seltzer | 139/413 |
| 3,183,910 | A | * | 5/1965 | Patterson | 604/381 |
| 3,543,756 | A | * | 12/1970 | Lee et al. | 604/374 |
| 3,794,033 | A | * | 2/1974 | Ryan | 604/365 |
| 3,811,445 | A | * | 5/1974 | Dostal | 604/375 |
| 4,216,773 | A | | 8/1980 | Ryan | |
| 4,361,151 | A | * | 11/1982 | Fitzgerald | 604/15 |
| 4,445,900 | A | * | 5/1984 | Roeder | 604/389 |
| 4,813,949 | A | * | 3/1989 | O'Rourke | 604/391 |
| 4,828,555 | A | * | 5/1989 | Hermansson | 604/379 |
| 4,886,513 | A | * | 12/1989 | Mason et al. | 604/385.31 |
| H1585 | H | * | 8/1996 | Ahr | 604/378 |

(Continued)

FOREIGN PATENT DOCUMENTS

EP 0 298 348 1/1989

(Continued)

OTHER PUBLICATIONS

Notification of the First Office Action issued in corresponding Chinese Patent Application No. 200480039582.9, dated Nov. 30, 2007.

(Continued)

*Primary Examiner*—Tatyana Zalukaeva
*Assistant Examiner*—Paula L Craig
(74) *Attorney, Agent, or Firm*—Buchanan Ingersoll & Rooney PC

(57) ABSTRACT

An absorbent article such as a sanitary towel, diaper, incontinence protector or panty liner, has a substantially elongated shape with a longitudinal direction and a transverse direction and has two side edges, a front edge and a rear edge, a front portion, a rear portion, and a middle portion located between the front portion and the rear portion. The article includes a shaping element. The shaping element includes at least two substantially elongated blanks which are cross-laid in an at least partially overlapping and substantially X-shaped configuration. A method for manufacturing an absorbent article permits improved manufacture of the article, with less material wastage.

4 Claims, 4 Drawing Sheets

U.S. PATENT DOCUMENTS

| | | | |
|---|---|---|---|
| 5,558,656 A * | 9/1996 | Bergman | 604/385.23 |
| 5,634,914 A * | 6/1997 | Wilkes et al. | 604/375 |
| 5,704,932 A * | 1/1998 | Hibbard | 604/387 |
| 6,013,065 A * | 1/2000 | Suzuki et al. | 604/385.27 |
| 6,179,820 B1 * | 1/2001 | Fernfors | 604/385.27 |
| 6,245,961 B1 * | 6/2001 | Roxendal et al. | 604/367 |
| 6,280,427 B1 * | 8/2001 | Maggiulli | 604/385.01 |
| 6,486,379 B1 * | 11/2002 | Chen et al. | 604/378 |
| 6,616,648 B2 * | 9/2003 | Hermansson et al. | 604/385.27 |
| 6,794,557 B1 * | 9/2004 | Klemp et al. | 604/378 |
| 6,840,925 B2 * | 1/2005 | Mishima et al. | 604/385.01 |
| 6,908,458 B1 * | 6/2005 | Sauer et al. | 604/385.16 |
| 6,936,038 B2 * | 8/2005 | Tears et al. | 604/385.04 |
| 7,015,370 B2 * | 3/2006 | Watanabe et al. | 604/378 |
| 7,087,044 B2 * | 8/2006 | Ohnishi | 604/385.01 |
| 7,156,832 B2 * | 1/2007 | Drevik et al. | 604/385.31 |
| 2002/0026168 A1 * | 2/2002 | Yagou et al. | 604/378 |
| 2002/0143311 A1 * | 10/2002 | Brisebois | 604/385.01 |
| 2002/0173762 A1 * | 11/2002 | Ishikawa et al. | 604/385.01 |
| 2003/0045852 A1 * | 3/2003 | Esselburn | 604/385.14 |
| 2003/0125699 A1 * | 7/2003 | Drevik et al. | 604/385.31 |
| 2004/0013847 A1 * | 1/2004 | Nakashita et al. | 428/73 |
| 2004/0030313 A1 * | 2/2004 | Watanabe et al. | 604/378 |
| 2004/0102751 A1 * | 5/2004 | Schueler, Jr. | 604/367 |
| 2004/0147381 A1 * | 7/2004 | Cervantes Gallego | 482/142 |
| 2005/0055000 A1 * | 3/2005 | Ohnishi | 604/367 |
| 2005/0055004 A1 * | 3/2005 | Turi et al. | 604/385.27 |
| 2005/0096615 A1 * | 5/2005 | Kuen et al. | 604/385.01 |
| 2005/0113777 A1 * | 5/2005 | Samuelsson et al. | 604/385.01 |

FOREIGN PATENT DOCUMENTS

| | | |
|---|---|---|
| WO | WO 98/37840 | 9/1998 |
| WO | WO 00/44326 | 8/2000 |
| WO | WO 02/45637 | 6/2002 |
| WO | WO 03/053301 | 7/2003 |

OTHER PUBLICATIONS

An English Translation of the Office Action in CO 06063421 dated Apr. 6, 2009.

* cited by examiner

ABSORBENT ARTICLE HAVING X-SHAPED SHAPING ELEMENT

CROSS REFERENCE TO RELATED APPLICATIONS

The present application claims the benefit of U.S. Provisional Application No. 60/533,075, filed in the United States on Dec. 30, 2003, the entire contents of which are hereby incorporated herein by reference.

FIELD OF THE INVENTION

The present invention relates to an absorbent article such as a sanitary towel, diaper, incontinence protector or panty liner, which article has a substantially elongated shape with a longitudinal direction and a transverse direction and has two side edges, a front edge and a rear edge, a front portion, a rear portion, and a middle portion located between the front portion and the rear portion, which article moreover comprises a shaping element.

The invention also relates to a method for manufacturing an absorbent article such as a sanitary towel, diaper, incontinence protector or panty liner, which article has a substantially elongated shape with a longitudinal direction and a transverse direction and has two side edges, a front edge and a rear edge, a front portion, a rear portion, and a middle portion located between the front portion and the rear portion, and also a shaping element.

BACKGROUND OF THE INVENTION

In connection with absorbent articles such as, for example, diapers, diaper pants, incontinence protectors for adults, sanitary towels and panty liners, there is a general requirement to provide materials and structures which are able to take up, distribute and absorb bodily excretions in a rapid and effective manner. Today's absorbent articles generally provide good absorption, with low risk of leakage, and a high degree of comfort for the person wearing the absorbent article.

A previously known absorbent article in the form of a sanitary towel is made up of a first cover sheet constituting a liquid-permeable top sheet, a second cover sheet constituting a liquid-impermeable bottom sheet, and an absorption body lying between these. The article can expediently be slightly cup-shaped to adapt to the female anatomy and to provide good contact against the body of a user. To give a further improved fit and liquid absorption capacity, today's sanitary towels are also often provided with a long and narrow longitudinal elevation extending up from the surface of the article. A sanitary towel can also be designed with an increased amount of absorption material at the area where liquid may be expected to be excreted.

An absorbent article of known type is disclosed in the document WO 02/45637 and is designed with a substantially elongated shape which defines a longitudinal direction and a transverse direction. The article comprises two side edges, a front edge and a rear edge, a front portion and a rear portion, and a middle portion positioned between the front portion and the rear portion. The known article further comprises a liquid-permeable top sheet, a liquid-impermeable bottom sheet, and an absorbent core. According to WO 02/45637, the absorbent core is designed with two "legs" which form a specific angle in relation to one another. Arranged between these "legs" there is an elastic element which causes a ridge-like elevation to be formed between the two legs.

It can further be stated that a sanitary towel is a mass-produced item which is manufactured in very large quantities, and there are ever increasing demands regarding a low manufacturing cost, low material consumption and low material wastage, combined with increased quality and improved function, not least as regards the absorbent core of the article.

U.S. Pat. No. 4,216,773 has already disclosed a method for manufacturing diapers in which a substantially rectangular absorption body is slit in a pattern defining fold lines which form flaps. These flaps are then folded in overlapping fashion across the middle part of the absorption body. In this way, a thicker section of material is obtained at the middle of the diaper in question by means of a simple and cost-effective manufacturing process.

Although the known types of absorbent articles described above may be regarded as having a satisfactory function, it can be stated that there is still a problem in the form of increased demands for further simplified manufacturing methods for the type of absorbent article in question, in particular permitting low material wastage and lower manufacturing costs in combination with a manufacturing process for the absorbent core.

OBJECTS AND SUMMARY

A main object of the present invention is to make available an improved absorbent article and an improved method for manufacturing an absorbent article in which the abovementioned problems are solved.

This object can be achieved with an article of the type mentioned in the introduction, which is characterized in that said shaping element preferably comprises at least two substantially elongated blanks which are cross-laid in an at least partially overlapping and substantially X-shaped configuration.

The object can also be achieved with a method of the type mentioned in the introduction, which is characterized in that it further preferably comprises producing at least two substantially elongated blanks which constitute said shaping element, and laying said blanks crosswise in an at least partially overlapping and substantially X-shaped configuration.

The embodiments of the invention afford certain advantages. In particular, it may be mentioned that the article according to embodiments of the invention can be manufactured with a very small amount of material wastage, which in turn gives lower production costs and less expensive products compared with the prior art.

BRIEF DESCRIPTION OF THE FIGURES

Embodiments of the invention will now be described with reference to a preferred embodiment and to the attached drawings, in which.

DETAILED DESCRIPTION OF PREFERRED EMBODIMENTS

Figure 1:
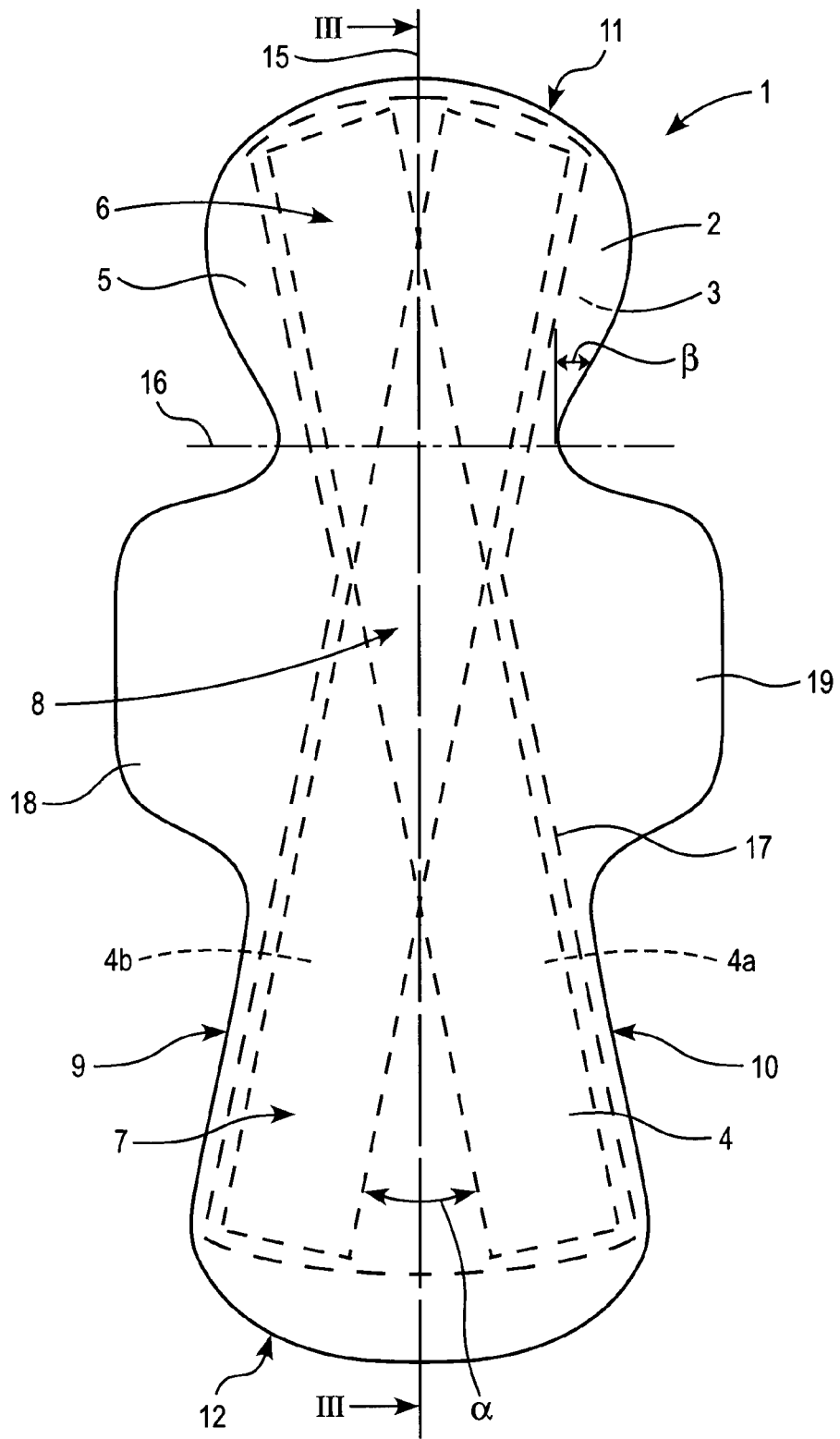
FIG. 1 shows a plan view of the absorbent article according to an embodiment of the invention.

An absorbent article 1 according to an embodiment of the present invention is shown in a plan view in FIG. 1. The article 1 according to the embodiment shown comprises a first cover sheet in the form of a liquid-permeable top sheet 2, which is arranged on that face of the article 1 which is intended to be directed towards the user during use. The article 1 also comprises a second cover sheet in the form of a liquid-impermeable bottom sheet 3 which is arranged on that face of the article 1 which is intended to be directed away from the user during use. The article 1 also comprises an absorbent core 4 arranged between the top sheet 2 and the bottom sheet 3. The absorbent core 4 is expediently made of a fibre sheet, preferably a strongly compressed fibre sheet. Alternative expedient materials are absorbent foam materials, sheets made of cellulose fluff pulp, wadding material, and other absorbent materials of types known per se which are suitable for use in, for example, sanitary towels, diapers for infants, incontinence protectors and panty liners.

The top sheet 2 and the bottom sheet 3 are joined together outside the absorbent core 4 and along the periphery of the article 1, for example by gluing, sewing, welding or some other suitable joining method, so that a peripheral edge 5 is formed.

The absorbent article 1 is substantially long and narrow and can be said to comprise a front portion 6, directed forwards on the user during use, and a rear portion 7, directed rearwards on the user during use. The article 1 additionally comprises an intermediate, relatively narrow portion 8 which is placed at a position corresponding to the groin area of a user. The article 1 also has two curved side edges 9, 10, a convexly curved front edge 11, and a convexly curve-shaped rear edge 12.

The division of the absorbent article 1 into a front portion 6, rear portion 7 and middle portion 8 should not be understood as meaning that there are sharply defined lines or borders between the different portions 6, 7, 8, and instead this primarily is intended to clearly explain the function of these different parts during use of the article 1, the portions 6, 7, 8 being placed at different positions in relation to the user's body. The transitions between the front portion 6 and the middle portion 8, and between the middle portion 8 and the rear portion 7, are thus not positioned at exact, predetermined boundary lines, but rather within transition areas which are located about a third of the way along the length of the article 1, calculated from the front edge 11 and from the rear edge 12, respectively. It can thus be stated that the middle portion 8 constitutes that part of the article 1 which, during use, is intended to admit and absorb most of the liquid excreted by the user to the absorbent article 1.

The absorption body 4 defines a shaping element which, according to the embodiment shown, constitutes an absorbent core which in turn is made up of two separate core blanks 4a, 4b, as can be seen from FIG. 1. The core blanks 4a, 4b are positioned in such a way that they form a substantially X-shaped configuration between the bottom sheet 3 and the top sheet 2, i.e. so that the core blanks 4a, 4b are laid crosswise such that they at least partially overlap one another. Upon manufacture of the article 1, the two core blanks 4a, 4b are thus arranged in the desired X-shaped configuration, after which they are fixed together with the other sheets 2, 3 included in the article 1. The resulting absorption body 4 will thus have the appearance shown separately in FIG. 2, i.e. with a width a in the front portion 6 which exceeds the width b in the middle portion 8. At the area where the two core blanks 4a, 4b overlap one another, the absorption body 4 will also have a thickness which corresponds approximately to twice the thickness of each individual separate core blank 4a, 4b.

The core blanks 4a, 4b also define two "legs" 13, 14 in the rear portion 7 of the absorbent article 1. These legs will extend rearwards and will define a certain predetermined angle α between the legs 13, 14. The choice of angle α and also the length of each leg 13, 14 (i.e. calculated from an imagined point of intersection between the legs 13, 14) can be adapted to the requirements regarding, for example, the fit and liquid-absorbing capacity of the article, i.e. how these properties are controlled by the positioning and dimensioning of the absorbent material in the absorption body 4. The angle α can be between 10° and 120°, preferably between 15° and 40°, and the length of each leg, calculated from said point of intersection, can be between 20 and 350 mm, preferably between 50 and 150 mm.

Figure 2:
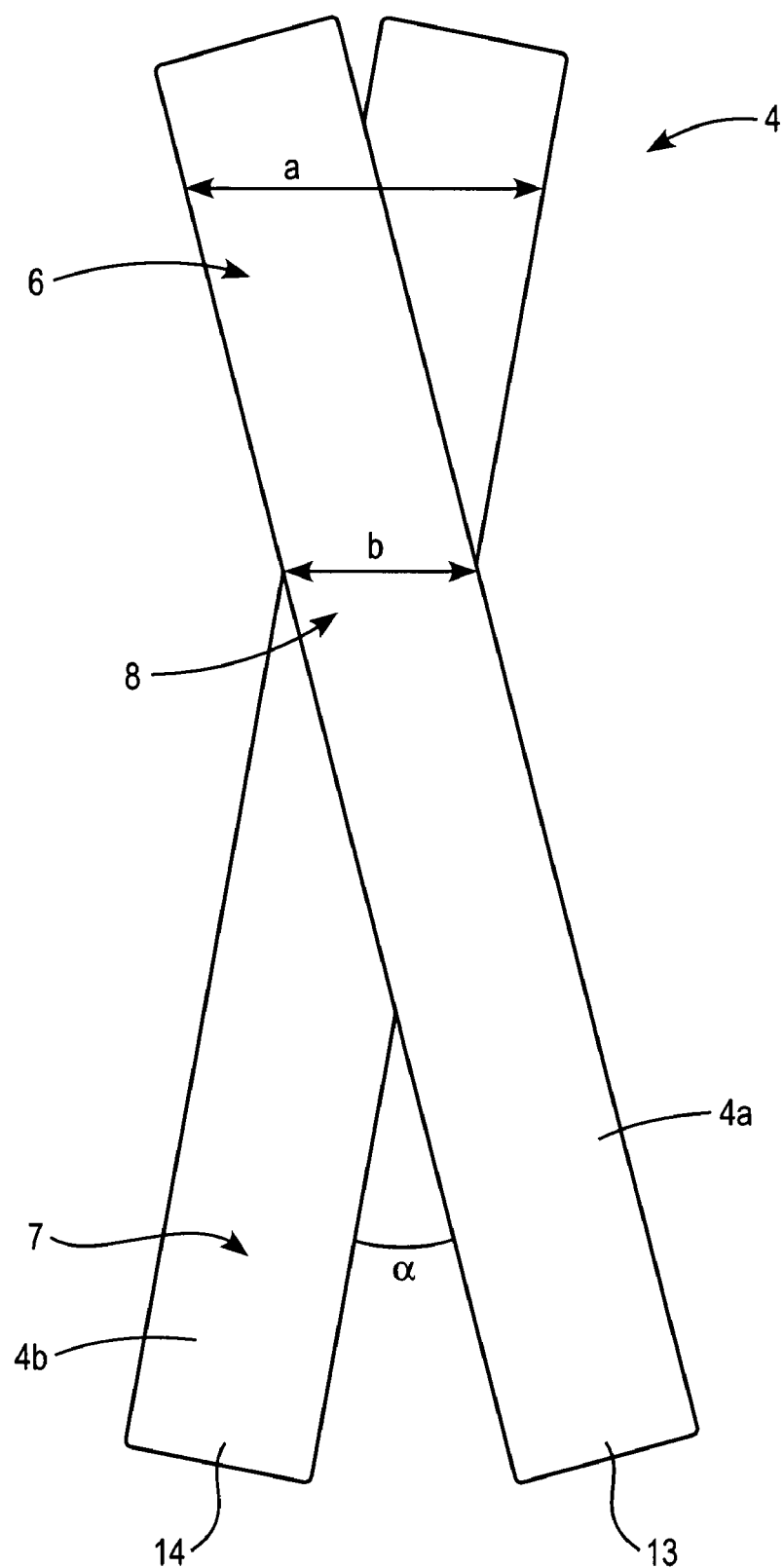
FIG. 2 shows a plan view of an absorbent core to be used in an embodiment of the invention.

As can be seen from FIG. 2, the absorbent article 1 according to the described embodiment of the invention is designed with a front portion 6 which is wider than the middle portion 8, and with a middle portion 8 which is narrower than both front portion and rear portion. To obtain an absorbent article which has a good fit and feels comfortable for the user, the sanitary towel may have a shape which to a large degree is adapted to the user's anatomy. It is thus preferable that the width b of the absorption body 4, at least in the front part of the middle portion 8, does not exceed about 40 mm. A reason why the front portion 6 is wider than the middle portion 8 is that the wider front portion 6, together with the narrower middle portion 8, shapes itself around the user's body and the absorbent article 1 to a certain extent "hitches" against the user's legs, thus making it possible for the absorbent article to remain in place against the user's body.

The slightly wider front portion 6 is preferably present in a slightly oval shape. A reason for this is that, when it is used, it is curved inwards as a cup shape is formed, i.e. the upward bending of the front portion 6, in relation to the middle portion 8, does not take place along a sharp fold line, and instead the curvature is continuous in the longitudinal direction of the absorbent article. In this way, the front portion 6 forms a gently rounded cup which adapts well to the user's anatomy. In addition, the oval shape of the front portion 6 also gives a large absorption area and a large volume for the absorption body 4.

Referring to FIG. 1, it will be noted that the absorbent article 1 is oriented in a longitudinal direction which is defined by a centre line 15. The article 1 also has two longitudinal side edges 9, 10, a transverse, convexly curved front edge 11, and a transverse convexly curved rear edge 12. The absorbent article is designed in such a way that in the front part of the middle portion 8 there is a first transverse line 16 which extends in the transverse direction of the absorbent article and which cuts through the side edges 9, 10 of the absorbent article. At the first transverse line 16, the side edges 9, 10 change inclination in relation to the longitudinal centre line 15, as a result of which the width of the absorbent article increases in the direction towards the front edge 11. In this way, the front portion 6 has a maximum width which exceeds the width of the middle portion 8 at the first transverse line 16.

The maximum width of the front portion 6 is preferably at least 1.5 times the width of the middle portion 8 at the first transverse line 16. The inclination of the side edges 9, 10 at the front portion 6 is defined by an angle β between each respective side edge 9, 10 and a longitudinal line which is parallel to the centre line 15, as a result of which β is preferably between 30° and 90°, and the width of the middle portion 8 of the absorption body 4 at the first transverse line 16 is preferably between 15 and 45 mm and preferably between 20 and 40 mm.

The article 1 is also designed with wing-like projections 18, 19 which, in a known manner, can be provided with suitable adhesive for securing the article 1 to underclothes during use.

According to the embodiment which is shown in FIGS. 1 and 2, the article 1 comprises a further sheet 17 which expediently consists of a further absorbent sheet. For example, the first absorbent sheet, i.e. the absorption body 4, can be a "fast" material which transports liquids, while the second absorbent sheet 17 can be then be formed so that it has a good ability to store liquids.

The further sheet 17 can be a stiffening material, i.e. it can be formed both with absorbent and with stiffening properties for the article 1. Alternatively, the further sheet 17 can provide stiffening but be essentially without absorbent properties, which is the case if, for example, it consists of a foam material essentially without absorbent properties.

According to a further variant of the invention, the article 1 can be formed so that the further sheet 17 consists of an absorbent sheet while the cross-laid structure 4a, 4b is a stiffening material. Analogously with what has been described above, the last-mentioned structure 4a, 4b can then provide stiffening with absorbent properties or can provide stiffening but without absorbent properties.

Figure 3:
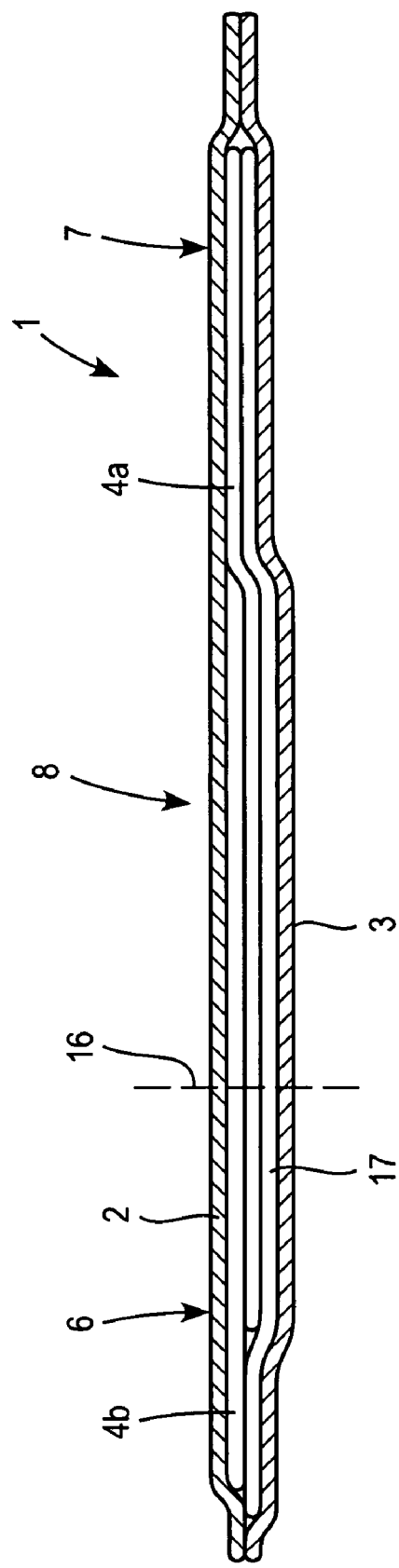
FIG. 3 shows a cross-sectional view of the article according to FIG. 1 along the line III-III in FIG. 1.

The further sheet 17 can be positioned under the cross-laid structure 4a, 4b, as can be seen in FIGS. 1 and 3. Alternatively, the cross-laid structure 4a, 4b can be positioned under the further sheet 17. According to a further alternative, the further sheet 17 can be positioned between the two cross-laid core blanks 4a, 4b.

It can generally be said that the structure indicated by reference number 4 in FIGS. 1-3 constitutes a stiffening element which is arranged with two or more blanks which is turn are laid out in a substantially X-shaped configuration. This shaping element 4 is preferably supplemented by a further sheet 17 in accordance with what has been described above. In the case where the further sheet 17 is a stiffening sheet, the stiffness of said sheet 17 can be suitably adapted to the shaping element. For example, the further sheet 17 can be produced in such a way that it becomes stiffer than the shaping element 4, for example by adhesive lamination of several sheets of identical or different materials or some other suitable production alternative.

The shape of the article 1 can also be seen clearly in FIG. 3, which is a cross-sectional view along line III-III in FIG. 1. It will be seen from FIG. 3 that the absorbent article 1 according to the invention has a middle portion 8 which is relatively thick, since the two core blanks 4a, 4b are cross-laid and thus overlap one another at said middle portion 8. This means that the middle portion 8 is given an increased absorption capacity compared with the absorption capacity of each of the individual core blanks 4a, 4b. FIG. 3 also shows the further sheet 17.

A manufacturing process for an absorbent article 1 according to an embodiment of the invention includes a step in which the absorption body 4 is arranged between the top sheet 2 and the bottom sheet 3. More specifically, the starting material for the absorption body 4 preferably consists of a rolled-up absorbent material. The two long narrow core blanks 4a, 4b are punched out from this material in the form of separate elements which together are to form the absorption body 4. The core blanks 4a, 4b are thereafter applied on the bottom sheet 3, after which the top sheet 2 is put in place and the whole article 1 is fixed in this configuration. When applying the core blanks 4a, 4b, they are laid out so that the abovementioned X-shaped configuration is formed. In this way, a thicker core of absorbent material is obtained where the core blanks 4a, 4b cross one another. The position of this relatively thick section is also adapted to the area of the article 1 where wetting may be expected during use. It is also true that the size of this relatively thick section depends on the choice of angle α between the legs 13, 14 (see FIG. 2) of each core blank 4a, 4b, but also on other parameters such as, for example, the width and thickness of the strip constituting the starting material for the absorption body 4. It may be noted here that a suitable width for each core blank 4a, 4b is of the order of 25 mm. However, in the case of the invention being applied in the form of a panty liner, this width can be less.

An important advantage of the above-described method of manufacture is that it generates minimal material wastage with respect to the absorbent article in question, and efficient formation of a relatively thick section in the middle portion 8 of the article 1. In addition, the two abovementioned legs 13, 14 are formed by the X-shaped configuration, and they in turn contribute to a high degree of mobility.

An alternative approach in the manufacture of the absorption body 4 is to use two separate material webs of absorbent material which are arranged so that, when they are applied on the bottom sheet 3, they are "cross-laid", i.e. advancing and placing the absorbent material directly in accordance with the X-shaped configuration. The first core blank 4a in this case originates from one material web, while the second core blank 4b originates from the second material web.

Figure 4:
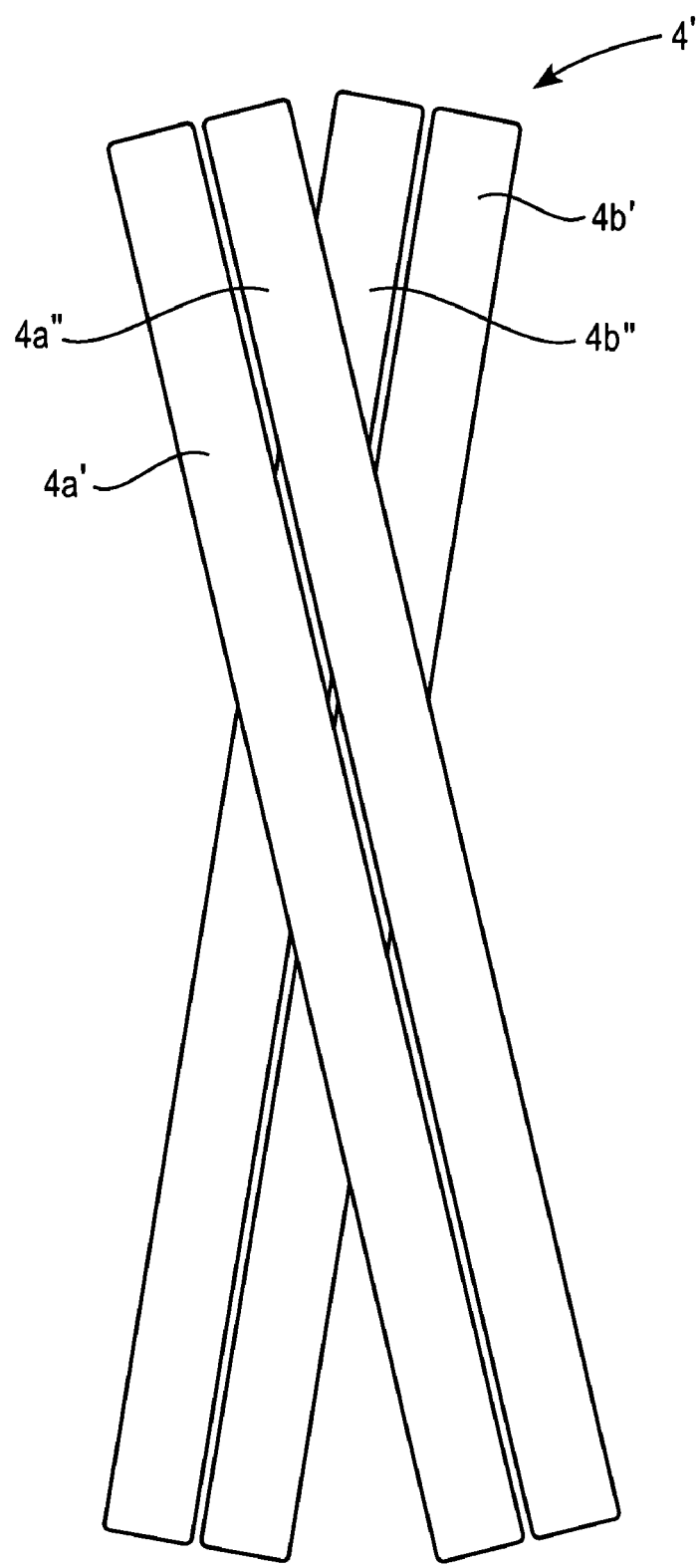
FIG. 4 shows a plan view of an absorbent core according to an alternative embodiment of the invention.

An alternative embodiment of the invention is shown in FIG. 4, which shows a plan view of a shaping element in the form of an absorbent core 4'. According to this embodiment, two relatively narrow blanks 4a', 4a" are used which are cross-laid with a further two relatively narrow blanks 4b', 4b". Otherwise, the absorbent core 4' according to FIG. 4 can have a corresponding application to the embodiments which have been described above. Dimensions such as width and length of each blank 4a', 4a", 4b', 4b" can be chosen depending on whether it is absorbent material or stiffening material that constitutes the cross-laid structure, and depending on whether the article in question will be, for example, a sanitary towel, diaper, incontinence protector or panty liner.

The material in the top sheet 2 can, for example, be a perforated plastic film, a plastic net or a textile material, a fibre wadding, a nonwoven material or a laminate of, for example, a perforated plastic film and a nonwoven sheet. The laminate can be made of any material suitable for the chosen purpose. The plastic material is normally a thermoplastic, such as polyethylene or polypropylene. The expression "non-woven material" refers to a nonwoven fibre fabric. Suitable nonwoven materials can consist of natural fibres, such as cellulose or cotton, or synthetic fibres such as polyethylene, polypropylene, polyester, polyurethane, nylon or regenerated cellulose. Of course, it is also possible to use nonwoven material produced from fibre mixtures.

The liquid-permeable top sheet 2 is intended to receive and convey the liquid into the absorption body 4. In addition, the top sheet 2 should be both soft and comfortable against the user's body and capable of preventing so-called rewetting, i.e. when absorbed body excretions force their way back towards the user's skin. For reasons of comfort, and to prevent skin irritation, it is important that the surface of the portion of the absorbent article in contact with the user's skin is kept as dry as possible during use. In addition, a dry surface of the absorbent article feels cooler and more comfortable to the user during use, and, from a purely visual point of view, and also when handling the absorbent article when it is being changed, this is more attractive than a soiled, wet surface. However, to avoid irritation of the mucosa of the genitals, those parts of the absorbent article in contact with the mucosa are preferably slightly moist.

The article 1 can further be provided with a suitable additive or lotion, with the aim of promoting skin contact between the article 1 and the user's body.

It is not necessary, in all the embodiments of the invention, for the top sheet 2 to constitute a separate material sheet. The top sheet can, for example, constitute an integral part of an absorbent body. It is thus conceivable that if the top sheet 2, i.e. the liquid-permeable cover sheet, is omitted, then the absorbent body should comprise an absorbent foam sheet or another absorbent material which is sufficiently cohesive so as not to separate during use. In addition, it is possible to use an absorbent nonwoven material, which material can be a component in an absorbent body and at the same time constitute a liquid-permeable top sheet.

The liquid-tight bottom sheet 3 may consist of a liquid-tight material. Thin, liquid-tight plastic films are suitable for this purpose. However, it is also possible to use material which is originally liquid-permeable but which has been provided with a surface coating of plastic, resin, or other liquid-tight material. In this way, leakage of liquid from the underside of the absorbent article is prevented. The liquid-tight bottom sheet 3 can consequently consist of any material which is skin-friendly and satisfies the criterion of being liquid-tight.

Examples of materials which are suitable as barrier sheets are plastic films, nonwoven materials and different types of laminates. Some plastic films that can be used are, for example, those consisting of polyethylene, polypropylene or polyester. Alternatively, the bottom sheet 3 can consist of a laminate made of a liquid-tight plastic sheet, directed towards the absorbent body, and of a nonwoven sheet directed towards the user's underclothes. Such a construction allows for a leakage-proof barrier sheet with a textile feel.

In the same way as with the top sheet 2, it is not necessary for the bottom sheet 3 to constitute a separate sheet. Consequently, it is conceivable for the bottom sheet 3 to constitute an integral part of an absorbent material, for example an absorbent foam material with a liquid-tight surface.

The absorption body 4 can advantageously consist mainly of cellulose fluff pulp. The pulp can be present in the form of reels, bales or sheets which are dry-shred or wet-formed and converted in a fluff state to a pulp mat, with or without admixture of so-called superabsorbents which are polymers having the ability to absorb several times their own weight of water or bodily excretions. Examples of other materials that can be used are various types of natural fibres such as cotton fibres, peat or the like. It is of course also possible to use absorbent synthetic fibres or mixtures of natural and synthetic fibres. The absorption material can further include additional components, such as liquid-distributing elements or binders such as, for example, thermoplastic fibres which have been heat-treated to bind together short fibres and particles into a coherent unit. It is also possible to use different types of absorbent foam material in the absorption body 4. Moreover, the absorption body 4 can be provided with odour-inhibiting means.

The invention is not limited to the above-described embodiment and instead it can be modified within the scope of the attached patent claims. For example, the invention is not limited to application to sanitary towels, and instead can also be used for other types of absorbent articles, for example diapers for infants, panty liners and incontinence protectors. The invention can generally be used for all types of absorbent articles whose sizes are adapted to substantially fit the groin area of a user.

According to the abovementioned embodiment, the two strips which form each core blank 4a, 4b are substantially the same width. Alternatively, however, they can have other dimensions and shapes, for example narrowing.

The dimensions which are chosen in accordance with the invention for the different components involved can vary depending on whether the invention is used as, for example, a sanitary towel, diaper, incontinence protector or panty liner.

Moreover, the article 1 can be provided with an elastic element (not shown) which is arranged between the two legs 13, 14 in the absorption body 4 and which is intended to draw the legs together and form a ridge-like elevation between the first leg 13 and the second leg 14. In this way, the fit can be enhanced and the risk of leakage rearwards along the article 1 is reduced. More specifically, such an elastic element can be placed between the legs as a continuous thread or a continuous band and is advantageously secured to the liquid-tight cover sheet 3.

It is however understood that the article described above and shown in the drawings only represents a non-limiting examples and that the present invention is not limited thereto, but can be used in any type of absorbent articles as defined above.

Although only preferred embodiments are specifically illustrated and described herein, it will be appreciated that many modifications and variations of the present invention are possible in light of the above teachings and within the purview of the appended claims without departing from the spirit and intended scope of the invention.

The invention claimed is:

1. An absorbent article having a substantially elongated shape with a longitudinal direction and a transverse direction and having two side edges, a front edge and a rear edge, a front portion, a rear portion, and a middle portion located between the front portion and the rear portion, the absorbent article comprising:
   an absorbent core comprising at least two substantially elongated absorbent core blanks having substantially similar dimensions, each formed of a sheet of absorbent material, which are cross-laid in an at least partially overlapping and substantially X-shaped configuration, wherein the absorbent core also functions as a shaping element which allows the front portion to shape itself around a user's body;
   a liquid-permeable cover sheet and a substantially liquid-tight cover sheet; and
   wherein an area of the core blanks where the core blanks at least partially overlap each other is positioned between the liquid permeable cover sheet and the substantially liquid-tight cover sheet;
   wherein said shaping element is a stiffening element;
   said shaping element comprises a portion at which said blanks cross one another and which corresponds to the middle portion of said article, the middle portion of the article being where wetting is expected during use;
   said shaping element is divided, at said rear portion, into a first leg and a second leg, each leg extending from said middle portion of said article, each leg forming a part of said substantially X-shaped configuration, with a gap between the legs where an angle is defined between the first leg and the second leg;
   said angle is between 15° and 40°;
   the length of each leg is between 50 and 150 mm, calculated from a point of intersection between said legs; and the entire absorbent core is positioned between the liquid permeable cover sheet and the substantially liquid tight cover sheet.

2. The absorbent article according to claim 1, wherein a second absorbent sheet is positioned between the at least two substantially elongated core blanks and the substantially liquid-tight cover sheet.

3. The absorbent article according to claim 1, wherein the at least two absorbent core blanks are formed of the same material.

4. The absorbent article according to claim 1, wherein the at least two absorbent core blanks extend along substantially an entire longitudinal length of the article.

* * * * *